United States Patent [19]

Luginbuhl

[11] Patent Number: Plant 7,618

[45] Date of Patent: Aug. 13, 1991

[54] APPLE TREE "VERMONT GOLD"

[76] Inventor: William H. Luginbuhl, 1559 Hinesburg Rd., South Burlington, Vt. 05403

[21] Appl. No.: 503,886

[22] Filed: Apr. 3, 1990

[51] Int. Cl.[5] ..... A01H 5/00

[52] U.S. Cl. ..... Plt./34

[58] Field of Search ..... Plt./34, 35

*Primary Examiner*—James R. Feyrer

[57] ABSTRACT

A new variety of apple tree characterized by:

(1) Large size fruit with a greenish yellow ground color changing to yellow with further ripening or storage and displaying a red cheek;

(2) Fruit with a thin, slightly waxy skin and fine, very juicy, crisp, yellowish-white flesh which is quite sweet with a good balance of acidity and flavor.

(3) Extended harvest period.

4 Drawing Sheets

SUMMARY

The present invention relates to a new distinct apple tree which I call "Vermont Gold". This new variety was originated by me from the seed of an open pollinated Red Delicious apple planted in 1976.

Scions of my new variety were top worked by cleft grafting on a bearing Golden Delicious tree. The first fruit from these grafts was harvested in 1981. Whip grafts were placed on *Malus robusta* in 1986 fruited in 1989. Bud grafts to seedling rootstock made in 1986 have grown vigorously but have not fruited. Bud grafts to M26 and MM106 made in 1988 have grown vigorously but have not fruited. The parent tree began bearing fruit in 1986 and has fruited each year since.

Examination of the original Vermont Gold apple tree and its progeny produced asexually have convinced me that my new variety is distinguished from all other varieties of which I am aware. It possesses the following unique combination of characteristics which are transmitted through succeeding propagations:

(1) Excellent appearance of fruit—Large size with a greenish yellow ground color changing to yellow with further ripening or storage and displaying a red cheek. The overall appearance is very attractive, quite distinct, and recognizable.

(2) Excellent dessert quality of fruit—A thin, slightly waxy skin, and fine, very juicy, crisp yellow-white flesh which is quite sweet with a good balance of acidity and flavor.

(3) Extended harvest period—After reaching marketable maturity the fruit maintains its high quality on the tree with little natural drop for an extended period of up to one month.

DETAILED DESCRIPTION

Figure 1:
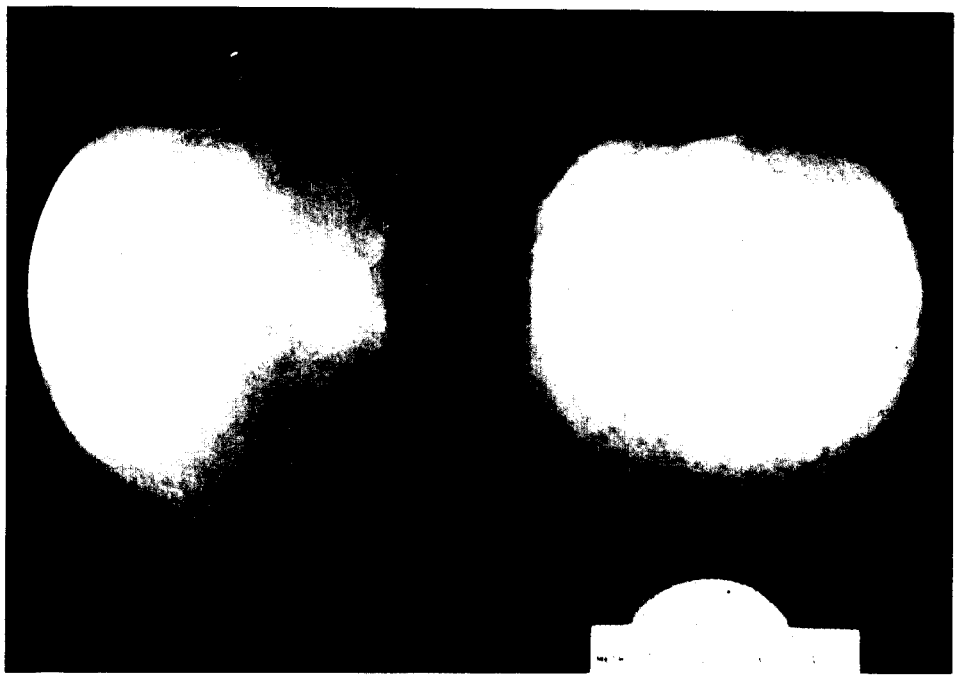
FIG. 1 is a photograph giving side views of fruit of the new variety of apple tree picked in early October.
Figure 2:
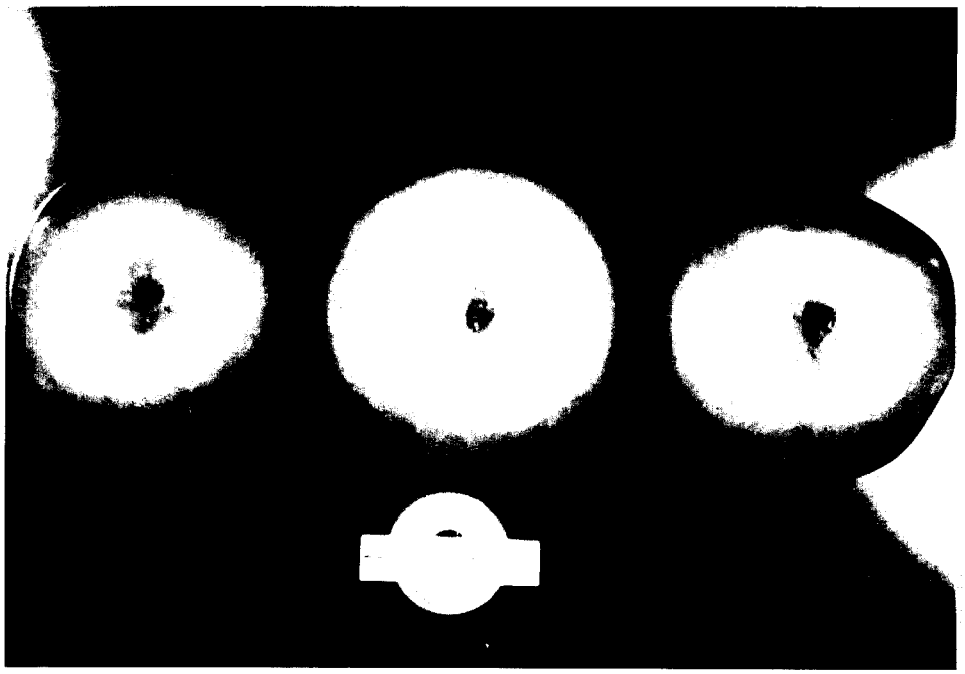
FIG. 2 is a photograph showing the basin of fruit of the new variety of apple tree.
Figure 3:
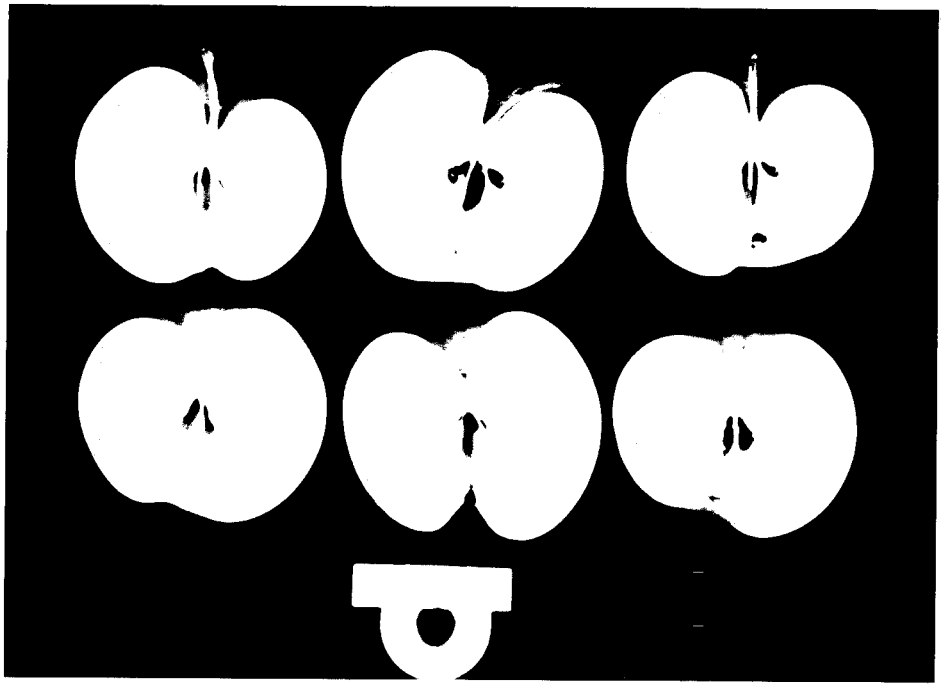
FIG. 3 is a photograph of longitudinal sections of fruit of the new variety of apple tree showing stem, cavity, open core, basin and calyx.
Figure 4:
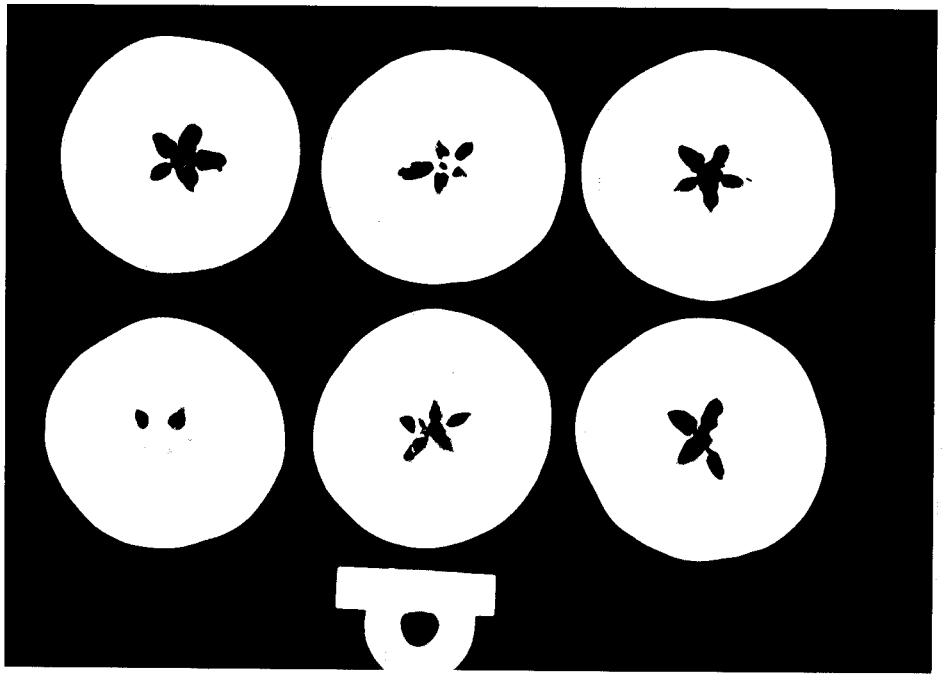
FIG. 4 is a photograph of transverse sections of fruit of the new variety of apple tree showing the open core and the seeds.
Figure 6:
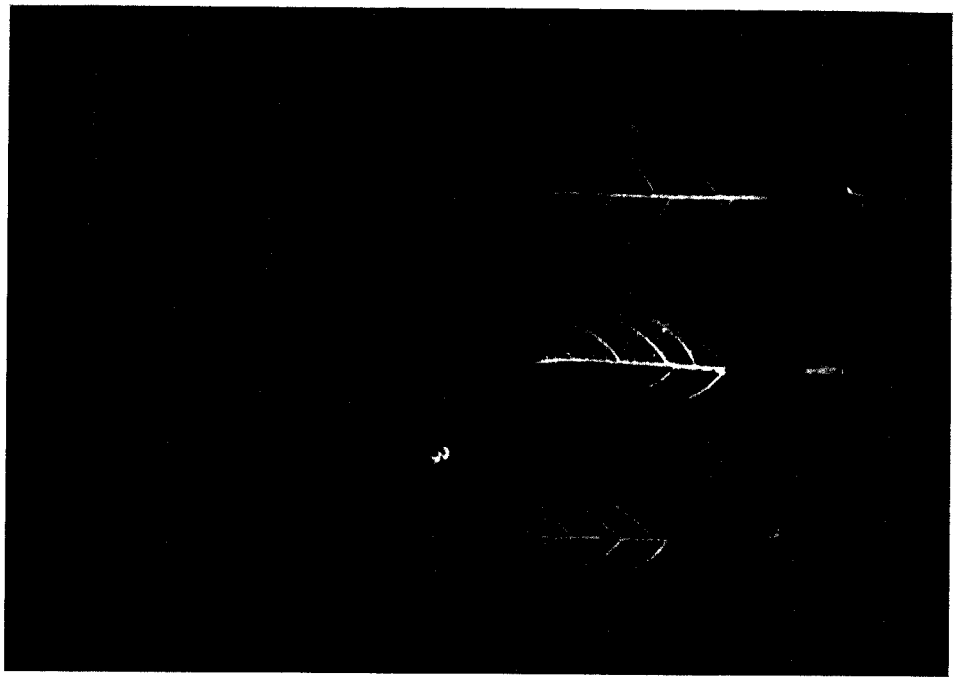
FIG. 6 is a photograph of the leaves of the new variety of apple tree showing the pubescent under surface (lower row) and the smooth upper surface (upper row).
Figure 5:
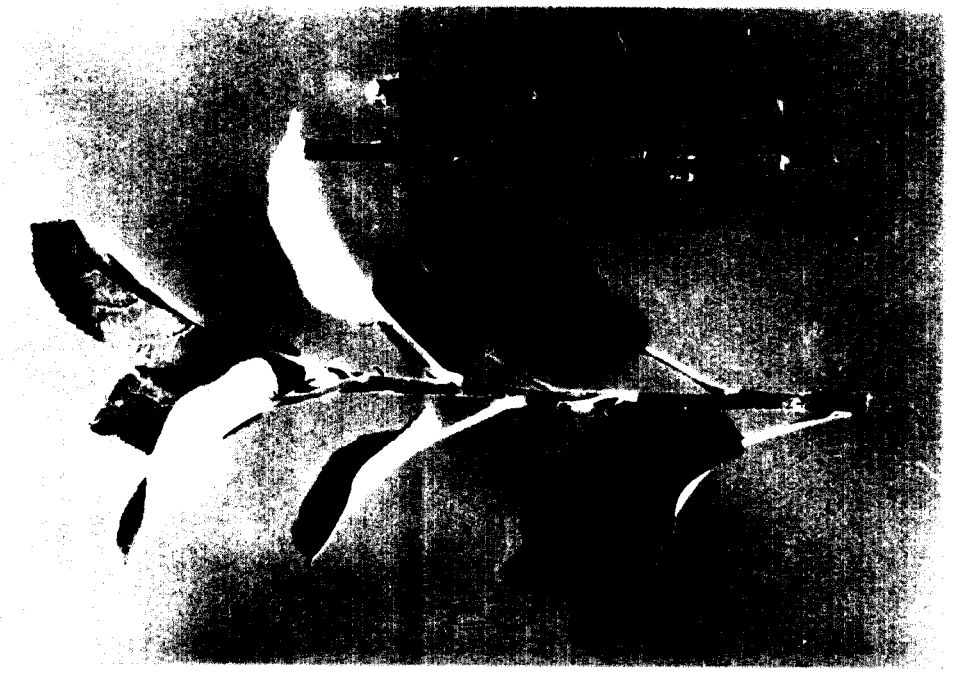
FIG. 5 is a photograph of the shoots of the new variety of apple tree showing pubescence of the shoot, the attachment of the leaves, the buds, stipules and leaf shape and margins.
Figure 7:
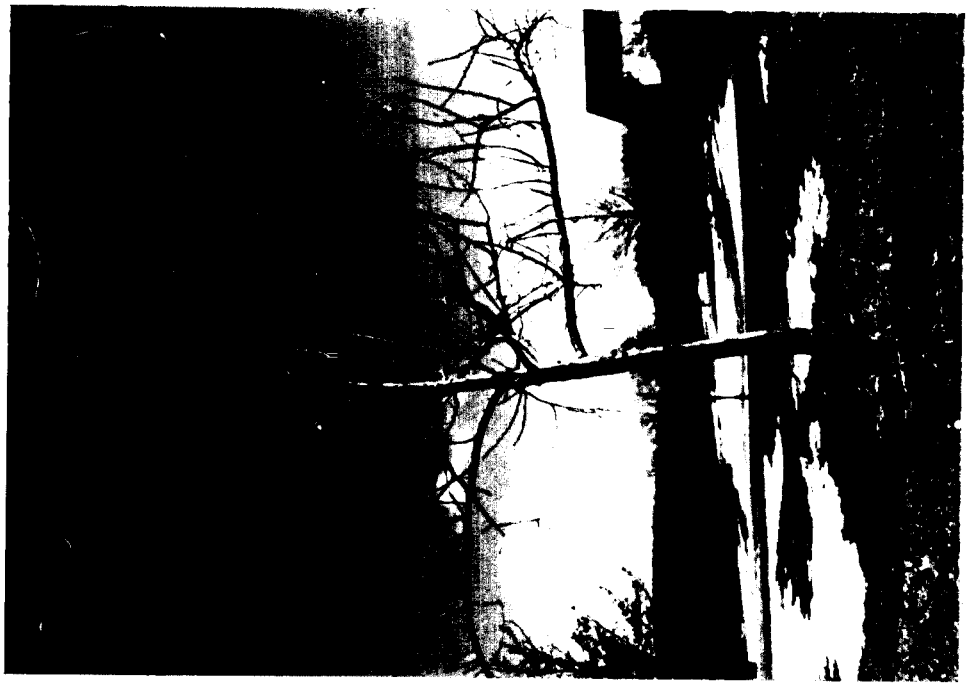
FIG. 7 is a photograph of the bare tree of the new variety described herein showing the upright pattern of growth and the size, placement and crotch angles of the branches.

Variety: Vermont Gold.

Parentage:

*Seed parent.*—Red Delicious.

*Pollen parent.*—Open pollinated.

Locality where grown and observed: South Burlington, Vt.

Dates of first and last pickings: Fruit of good tart quality may be picked 10 days to 2 weeks before McIntosh. There is little dropping for 4 to 5 weeks with fruit increasing in sweetness and decreasing in tartness. The peak of quality is the end of September at South Burlington, Vt. This is about one week after McIntosh.

Tree:

*Vigor.*—Growth rate vigorous, not a dwarf.

*Hardiness.*—Has withstood −25° F. without winter injury.

*Form.*—Upright, branches well placed; normal pruning results in strong, well-developed scaffold branches with wide crotch angles; overall form not atypical.

*Bearing habit.*—Normal, not a spur type; bears annually; crops are often moderately heavy and require thinning to allow development of maximum fruit size.

Shoot growth: Brown with grey pubescence on present season wood; two year old wood smooth with conspicuous lenticles.

Lenticles: White to grey, small (1 mm or less) quite numerous.

Leaf: Upper surface dark green, lower surface lighter green, pubescent, medium density; elliptic with accuminate tip, margin serrate, petiole medium length.

Flowers: Not atypical; blooms with midseason varieties.

Fruit: Size medium (200 gm) to large (250 gm).

Susceptibility to disease: Moderately susceptible to apple scab.

Shape: Slightly ribbed or angular, round-oblate, slightly to moderately asymmetric.

Cavity: Acute, narrow in width, deep; skin in cavity occasionally slightly russeted; some furrowing of the contour of the skin.

Stem: Leaning, medium long (15–20 mm), medium thick with some clubbing of twig end. Occasional specimen with short (1 cm) thick (4 mm) stem.

Basin: Deep, medium to wide, abrupt, irregular with sides ridged to wavy. Larger specimens with mammiform projections.

Calyx: Slightly to partially open, calyx lobes erect convergent green with brown tips.

Skin: Smooth, very thin, slightly waxy, tender.

Color: Ground color green yellow to yellow (R.H.S. 1 C to 4 B with ripening) with a grayed-red (R.H.S. 180 B) cheek.

Dots: Inconspicuous, small, moderate number, green to greenish-brown except occasionally pale in red blush areas.

Core lines: Meeting calyx tube near base; core medium to distant.

Locules (carpels): Elliptical; core open.

Flesh: Yellowish-white, very crisp, very juicy, sweet, subacid; flavor excellent for dessert.

I claim:

1. A new and distinct variety of apple tree, "Vermont Gold", substantially as shown and described.

* * * * *